United States Patent …

(12) United States Patent
Boettger et al.

(10) Patent No.: US 8,647,641 B2
(45) Date of Patent: Feb. 11, 2014

(54) MYCOBACTERIUM TUBERCULOSIS VACCINE

(75) Inventors: Erik Boettger, Zürich (CH); Peter Sander, Zürich (CH)

(73) Assignee: University of Zurich, Zurich (CH)

( * ) Notice: Subject to any disclaimer, the term of this patent is extended or adjusted under 35 U.S.C. 154(b) by 0 days.

(21) Appl. No.: 13/121,215

(22) PCT Filed: Oct. 9, 2009

(86) PCT No.: PCT/EP2009/007260
§ 371 (c)(1),
(2), (4) Date: Mar. 28, 2011

(87) PCT Pub. No.: WO2010/046039
PCT Pub. Date: Apr. 29, 2010

(65) Prior Publication Data
US 2011/0177120 A1    Jul. 21, 2011

(30) Foreign Application Priority Data
Oct. 20, 2008    (EP) .................... 08018304

(51) Int. Cl.
*A61K 39/04*    (2006.01)

(52) U.S. Cl.
USPC ...................... 424/248.1; 424/823

(58) Field of Classification Search
None
See application file for complete search history.

(56) References Cited

PUBLICATIONS

Master, S. S., et al. *Mycobacterium tuberculosis* prevents inflammasome activation. Cell Host Microbe. 2008. 3(4):224-32.*
Master SS et al. *Mycobacterium tuberculosis* prevents inflammasome activation. Cell Host Microbe. Apr. 17, 2008;3(4):224-32.*
Stover CK et al. New use of BCG for recombinant vaccines. Nature. Jun. 6, 1991;351(6326):456-60.*
Turner J et al. Effective preexposure tuberculosis vaccines fail to protect when they are given in an immunotherapeutic mode. Infect Immun. Mar. 2000;68(3):1706-9.*
Satria A. Prabowo et al. Targeting multidrug-resistant tuberculosis (MDR-TB) by therapeutic vaccines. Med Microbiol Immunol (2013) 202:95-104.*
Asensio et al. Live tuberculosis vaccines based on phoP mutants: a step towards clinical trials. Expert Opin Biol Ther. Feb. 2008;8(2):201-11. doi: 10.1517/14712598.8.2.201 . Review.*
International Search Report for International Application No. PCT/EP2009/007260, with a mailing date of Feb. 1, 2010, two (2) pages.
Master, Sharon S. et al., "*Mycobacterium tuberculosis* Prevents Inflammasome Activation", Cell Host & Microbe, 2008, pp. 224-232, vol. 3.
Stover, C.K. et al., "New use of BCG for recombinant vaccines", Nature, 1991, pp. 456-460, vol. 351.

* cited by examiner

*Primary Examiner* — Mary E Mosher
*Assistant Examiner* — Nick Zou
(74) *Attorney, Agent, or Firm* — Nath, Goldberg & Meyer; Lakshmi Rajan; Tanya E. Harkins

(57) ABSTRACT

The present invention relates to the use of live mycobacterium of the *M. tuberculosis* complex for preparing a medicament, wherein the function of the zmp1-gene is inactivated, pharmaceutical compositions prepared from such mycobacteria as well as a method for the treatment and/or prophylaxis of a disease or medical condition using said pharmaceutical composition.

5 Claims, 2 Drawing Sheets

MYCOBACTERIUM TUBERCULOSIS VACCINE

Figure 1:
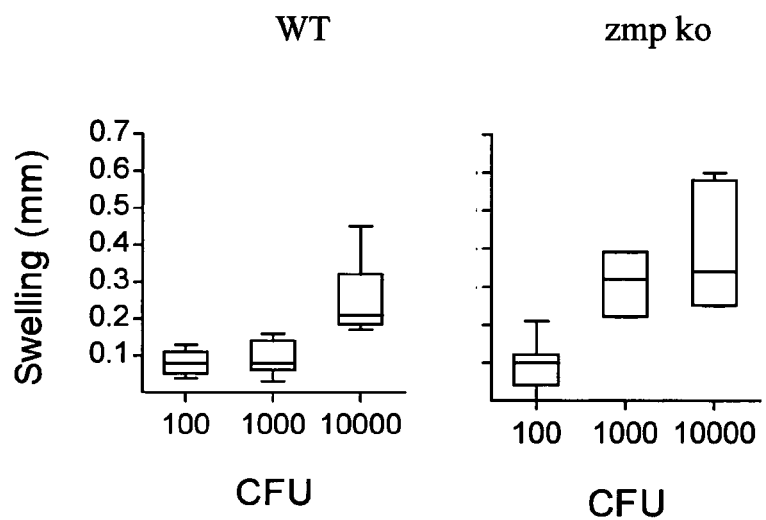

This is a National Phase Application filed under 35 U.S.C. §371 as a national stage of PCT/EP2009/007260, filed on Oct. 9, 2009, an application claiming the benefit under 35 U.S.C. §119 of European Patent Application No. 08018304.9, filed on Oct. 20, 2008, the content of each of which is hereby incorporated by reference in its entirety.

FIELD OF THE INVENTION

The present invention relates to the use of live mycobacterium of the *Mycobacterium tuberculosis* complex for preparing a medicament, wherein the function of the zmp1 gene (zinc metalloprotease 1 gene) is inactivated, pharmaceutical compositions prepared from such mycobacteria as well as a method for the treatment and/or prophylaxis of a disease or medical condition using said pharmaceutical composition.

BACKGROUND OF THE INVENTION

*Mycobacterium tuberculosis* is one of the most successful pathogens known today, killing millions of individuals worldwide every year. A hallmark of *M. tuberculosis* infection is that following phagocytosis the microorganisms resist lysosomal delivery, instead residing within phagosomes that do not fuse with lysosomes. Phagolysosomes are equipped with the machinery to generate peptide—MHC II complexes. Inhibition of phagolysosome fusion has been proposed to represent a mechanism by which *M. tuberculosis* escapes efficient antigen presentation by host MHC II complexes. In addition, cross-presentation of peptides derived from particulate antigens and exploiting the conventional MHC I pathway can occur via a putative phagosome-to-cytosol mechanism. Alternatively, this can occur by fusion and fission of phagosomes with endoplasmic reticulum-derived vesicles containing newly synthesized MHC I molecules.

BCG is a live attenuated vaccine derived from *M. bovis* back in 1919. More than three billion doses of the vaccine have been administered worldwide. Although BCG is relatively safe and inexpensive, its efficacy is highly variable (Fine, P. E. M., *Lancet* 346, 1339-1345, 1995). The reasons for the varying efficacy of BCG in protection against tuberculosis are poorly understood. One explanation builds on the observation that BCG has lost important genes during the laboratory attenuation process (Behr et al., *Nature* 389, 133-134, 1997). A great deal of work has been done to improve—with varying success—the efficacy of BCG by introducing additional copies of existing genes (Horwitz et al., *PNAS, USA* 97, 13853-13858, 2000) or by reintroducing some of the genes that were lost during the in vitro attenuation process (Pym et al., *Nat. Med.* 9, 533-539, 2003).

Alternative live vaccination strategies focus on attenuated *M. tuberculosis*. It is commonly assumed that tuberculosis disease will protect, at least partially, against subsequent reinfection. However, the failure of natural disease to protect against re-infection disease at a later point indicates that immunity evoked by natural infection is limited, partially explaining the relative ineffectiveness of vaccination with BCG. The limited post-infectious immunity may also indicate that *M. tuberculosis* actively escapes immune surveillance.

Recently, the present inventors reported that a putative mycobacterial zinc metallo-protease, Zmp1, may play an important role in disease pathogenesis by interfering with two pathways of pathogen defense: inflammasome activation and phagosome maturation (Master et al., *Mycobacterium tuberculosis* prevents inflammasome activation. *Cell Host Microbe* 3, 224-232, 2008).

It is the object of the present invention to provide a live mycobacterium-based medicament with increased immunogenicity and improved protective efficacy.

This object is solved by the use of at least one live mycobacterium of the *M. tuberculosis* complex for preparing a medicament, wherein the function of the zmp1-gene is at least partially inactivated, preferably inactivated.

It was found that live mycobacteria, wherein the function of the zmp1-gene is at least partially inactivated, preferably substantially or fully inactivated, elicit an increased immunogenicity and protective efficacy when compared to zmp1 active mycobacteria.

The term live mycobacterium of the *M. tuberculosis* complex as used herein refers to a mycobacterium species or strain which is a member of the *M. tuberculosis* complex, which includes but is not limited to *M. tuberculosis, M. bovis* BCG, *M. bovis, M. africanum* and *M. microti*.

Preferably, a mycobacterium of *M. bovis*, preferably *M. bovis* BCG, or *M. tuberculosis* is used for preparing a medicament according to the invention.

The mycobacterium used for the invention is alive, i.e. capable of propagation in a host, in particular in a mammalian host, preferably in a human host.

It is self-evident, that live mycobacteria for medical use must be attenuated to a degree not harmful to patients in need thereof. Hence, the mycobacterium used for the invention is preferably non-virulent, i.e. the genes responsible for virulence have been inactivated, and does not evoke or at least evokes minor disease symptoms of a mycobacterial infection in a mammal, preferably human.

Mycobacteria of the *M. tuberculosis* complex produce endogenous antigens which are cross-reactive with *M. tuberculosis*. Antibodies raised against such cross-reactive antigen will also bind specifically to one or more antigens from *M. tuberculosis* and are capable of evoking and/or potentiating an immune response against *M. tuberculosis* infection in a mammal. For example, cross reactive antigens of *M. bovis* BCG will evoke and/or potentiate an immune response against *M. tuberculosis*.

Mycobacteria of the *M. tuberculosis* complex are not only useful for expressing cross-reactive antigens but also have applications as a delivery system for the expression of exogenous or foreign antigens and/or immunogens. The efficacy of this delivery system lies in the long persistence in the immunized host (Stover et al., *Nature,* 351, 456-460, 1991; Aldovini and Young, *Nature,* 351, 479-482, 1991).

Exemplary suitable antigens for delivery via mycobacteria of the *M. tuberculosis* complex include viral, protozoal, tumour cell-derived, bacterial and fungal antigens. For example, antigens derived from *H. pylori*, measles virus, mumps virus, rubeola virus, *B. burgdorferi* (e.g. OspA), herpes virus, papilloma virus, *Pneumococcus* spp (e.g. surface protein A), tumour cells, leishmania (e.g. surface proteinase gp63), HIV or SIV may be used. Such an antigen may be useful in the treatment of ulcers, measles, mumps, rubeola, lyme disease, herpes, cancer, tetanus, diphtheria, leishmaniasis or AIDS.

In a preferred embodiment, mycobacteria for use in the present invention may also comprises genetic material encoding an antigen and/or immunogen exogenous or foreign to the mycobacterium. More preferably, the exogenous or foreign antigen and/or immunogen is selected form the group consisting of viral, protozoal, tumor cell-derived, bacterial and fungal antigens and immunogens, preferably selected from the group consisting of antigens and/or immunogens from *H. pylori*, measles virus, mumps virus, rubeola virus, *B. burgdorferi*, preferably protein ospA of *B. burgdorferi*, herpes virus, papilloma virus, *Pneumococcus* spp, preferably protein A of *Pneumococcus* spp., tumour cells, leishmania, preferably surface proteinase gp63 of leishmania, HIV and SIV.

Hence, the mycobacterium for use in preparing a medicament according to the invention is useful for the prophylaxis and/or treatment of diseases or medical conditions affected by antigen and/or immunogen expression of the mycobacterium. An antigen evokes antibody production in a host, an immunogen affects the immune system of a host.

Most evident as well as most preferred, the medicaments prepared from zmp1-inactivated mycobacteria according to the invention are useful for the prophylaxis and/or treatment of mycobacterial infections, preferably an infection of *M. tuberculosis*.

In a further preferred embodiment the present invention is directed to the use according to the invention for the prophylaxis and/or treatment of a disease or medical condition selected from the group consisting of ulcers, measles, mumps, rubeola, lyme disease, herpes, cancer, tetanus, diphtheria, leishmaniasis and AIDS.

One or more live mycobacteria species and/or strains with an at least partially inactivated zmp1-gene function can be used for preparing a medicament according to the invention.

The term "function of the zmp1-gene" as used herein is intended to mean the function of the putative mycobacterial zinc metalloprotease Zmp1 in inflammasome activation, caspase-1-dependent activation and secretion of IL-1β as well as phagosome maturation in mammalian, in particular human macrophages.

Hence, the function of the zmp1-gene in a mycobacterium can be directly verified and/or quantified by investigating inflammasome activation, caspase-1-dependent activation and/or secretion of IL-1β and/or phagosome maturation in mammalian, in particular human macrophages upon infection with the mycobacterium of interest. Of course, other direct and indirect effects of protein Zmp1, e.g. effects resulting from IL-1β activation and/or secretion, are also indicative of the function of the zmp1 gene and may also be used instead of or in addition to the above direct indicators.

The term "at least partially inactivated", as used herein, is meant to indicate a loss of zmp1 gene function directly and/or indirectly attributable to the expression of the zmp1 gene. Of course, the inactivation and extent of inactivation can best be determined in direct comparison to a mycobacterium of the same strain under identical experimental conditions but comprising a fully functional and expressed zmp1 gene. Preferably, "at least partially inactivated" relates to a loss of more than 10%, preferably more than 50%, more preferably more than 70%, most preferably more than 90% of a function directly and/or indirectly attributable to the expression of the zmp1 gene in a mycobacterium.

Partial and/or full inactivation of genes in mycobacteria of the *M. tuberculosis* complex for use in the present invention can be achieved by any conventional method in the art of gene mutation, e.g. recombinant insertion, replacement, deletion, frameshift and/or homologous recombination. Suitable specific methods for partially and/or fully inactivating genes, in particular the zmp1 gene in mycobacteria are described in WO 02/50262 (recA mutants), Master et al., supra, and the examples below.

It was found that the threshold for the induction of an immune response to *M. tuberculosis* antigens in immunized mammals was ten times less for mammals immunized with zmp1-deficient mycobacterial strains when compared to the threshold necessary for inducing the immune response in mammals immunized with the corresponding wild type, i.e. zmp1 activated, mycobacterial strain. Consequently, medicaments prepared from mycobacteria according to the invention evoke a substantially increased immunogenicity associated with increased proliferative and cytokine secreting immune responses.

Furthermore, the protective efficacy of mammals immunized with a medicament, i.e. pharmaceutical composition/vaccine, prepared according to the invention against *M. tuberculosis* challenge was demonstrated to be clearly superior over the protective efficacy achieved in mammals immunized with the corresponding wild type mycobacterial strain. In comparison, mammals immunized according to the invention demonstrated upon *M. tuberculosis* challenge a more pronounced and more frequent lymphocytic infiltration into lungs.

Last but not least, increased immunogenicity and protective efficacy of medicaments prepared according to the invention manifests itself in a substantially prolonged mean survival time of immunized mammals upon challenge with virulent *M. tuberculosis*.

Consequently, the medicaments prepared according to the invention present a significant improvement for therapeutic, prophylactic and other medical or veterinary applications of mycobacteria for delivering endogenous, exogenous and/or foreign antigens and/or immunogens to a mammal in need thereof.

A second aspect of the present invention concerns pharmaceutical compositions comprising as active substance at least one live mycobacterium of the *M. tuberculosis* complex, wherein the function of the zmp1-gene is at least partially inactivated, preferably inactivated, optionally and preferably combined with pharmaceutically acceptable conventional excipients and/or carriers.

A pharmaceutical composition according to the present invention is any composition, preferably a vaccine, formulated for direct medical administration to a patient in need thereof, preferably a mammal, more preferably a human.

Preferably, the mycobacterium in the pharmaceutical composition is *M. bovis*, preferably *M. bovis* BCG, or *M. tuberculosis*. It is also preferred that the mycobacterium used is non-virulent.

In a preferred embodiment the pharmaceutical composition according to the invention is one, wherein the mycobacterium comprises genetic material encoding an antigen and/or immunogen exogenous or foreign to the mycobacterium, wherein the antigen and/or immunogen is preferably selected form the group consisting of viral, protozoal, tumor cell-derived, bacterial and fungal antigens and immunogens, more preferably selected from the group consisting of antigens and/or immunogens derived from *H. pylori*, measles virus, mumps virus, rubeola virus, *B. burgdorferi*, preferably protein ospA of *B. burgdorferi*, herpes virus, papilloma virus, *Pneumococcus* spp, preferably protein A of *Pneumococcus* spp., tumour cells, leishmania, preferably surface proteinase gp63 of leishmania, HIV and SIV.

Preferably, the pharmaceutical composition according to the invention is one suitable for the prophylaxis and/or treatment of a disease or medical condition affected by antigen and/or immunogen expression of the mycobacterium, more preferably the prophylaxis and/or treatment of mycobacterial infections, preferably an infection of *M. tuberculosis*, also more preferably for the prophylaxis and/or treatment of a disease or medical condition selected from the group consisting of ulcers, measles, mumps, rubeola, lyme disease, herpes, cancer, tetanus, diphtheria, cancer, leishmaniasis and AIDS.

METHODS OF USE

The medicaments, i.e. pharmaceutical compositions, vaccines, etc. are useful for a method for medical treatment and/or prophylaxis. Consequently, in a further aspect the present invention relates to method for the treatment and/or prophylaxis of a disease or medical condition comprising the step of administering a pharmaceutical composition according to the invention to a mammalian, preferably a human patient in need thereof.

In a preferred aspect, the present invention is directed to the above method, wherein the disease and/or medical condition is selected from the group consisting of mycobacterial infections, preferably an infection of *M. tuberculosis*, ulcers, measles, mumps, rubeola, lyme disease, herpes, cancer, tetanus, diphtheria, cancer, leishmaniasis and AIDS.

For therapeutic and/or prophylactic use the pharmaceutical compositions of the invention may be administered in any conventional dosage form in any conventional manner. Routes of administration include, but are not limited to, intravenously, intramuscularly, subcutaneously, intranasally, intrasynovially, by infusion, sublingually, transdermally, orally, topically, or by inhalation. The preferred modes of administration are subcutaneous, intravenous and intranasal.

The mycobacteria may be administered alone or in combination with adjuvants that enhance stability and/or immunogenicity of the mycobacteria, facilitate administration of pharmaceutical compositions containing them, provide increased dissolution or dispersion, increase propagative activity, provide adjunct therapy, and the like, including other active ingredients.

As mentioned above, pharmaceutical dosage forms of the mycobacteria described herein include pharmaceutically acceptable carriers and/or adjuvants known to those of ordinary skill in the art. These carriers and adjuvants include, for example, ion exchangers, alumina, aluminium stearate, lecithin, serum proteins, buffer substances, water, salts, electrolytes, cellulose-based substances, gelatine, water, pretrolatum, animal or vegetable oil, mineral or synthetic oil, saline, dextrose or other saccharide and glycol compounds such as ethylene glycol, propylene glycol or polyethylene glycol, antioxidants, lactate, etc. Preferred dosage forms include tablets, capsules, solutions, suspensions, emulsions, reconstitutable powders and transdermal patches. Methods for preparing dosage forms are well known, see, for example, H. C. Ansel and N. G. Popovish, Pharmaceutical *Dosage Forms and Drug Delivery Systems*, 5$^{th}$ ed., Lea and Febiger (1990) and, in particular, Pastoret et al., Verterinary Vaccinology, Elsevier March 1999). Dosage levels and requirements are well-recognized in the art and may be selected by those of ordinary skill in the art from available methods and techniques suitable for a particular patient. As the skilled artisan will appreciate, lower or higher doses may be required depending on particular factors. For instance, specific doses and treatment regimens will depend on factors such as the patient's general health profile, the severity and course of the patient's disorder or disposition thereto, and the judgment of the treating physician.

For example, the pharmaceutical composition of the present invention can be administered the same way as conventional pharmaceutical compositions based on live mycobacteria or based on other bacteria.

In a preferred embodiment, a pharmaceutical composition comprises live bacteria of *M. bovis* BCG zmp1.

More preferably, the mycobacteria are lyophilized and stabilized with typical stabilizing agents such as sugars, e.g. sucrose, and/or gelatins. The pharmaceutical composition may be formulated into tablets or other solid forms and may be later reconstituted with water into a solution for administration, e.g. orally, by injection or intranasally.

It is emphasized that the pharmaceutical compositions of the present invention may be administered in lower dosages than conventional pharmaceutical compositions based on live mycobacteria because the mycobacteria used by the present invention are more immunogenic and evoke an improved protective efficacy when compared to compositions with conventional mycobacteria, e.g. wild type *M. bovis* BCG.

In the following the present invention will be illustrated in more detail with reference to specific embodiments which are not to be interpreted as limiting the scope of the invention as defined by the appended claims.

FIGURES

FIG. 1: Groups of C57BL/6 mice were immunised with 100, 1000 or 10000 CFU BCG WT or BCG zmp1 and challenged intradermally with PPD in the footpad on day 21. Footpad DTH was then measured after 48 hrs.

FIG. 2: Groups of C57BU6 were immunised with 1000 BCG WT (open bars) or BCG zmp1 (filled bars). After 4 weeks, splenocytes were restimulated in vitro with PPD, or Ag85A or TB10.3 peptides. IFN-g secretion (ELISA) and proliferation (3H-thymidine incorporation) were measured on day 3 and 4, respectively. * $p<0.05$,  $p<0.01$, * $p<0.001$ (Mann Whitney).

FIG. 3: Analysis of IFN-g producing CD4 and CD8 positive T cells following vaccination of mice with BCG WT, BCG zmp1 or saline (untr). Splenocytes were restimulated with PdBu or PPD and intracellular IFN-g analysed by flow cytometry. (A) Histograms show the frequency of IFN-g-producing CD8 T cells (mean±s.e.). (B, C) Box plots show the frequency of IFN-g-producing CD8 (B) or CD4 (C) T cells. The boxes show the 25$^{th}$ and the 75$^{th}$ percentile as wells as median, while the whiskers show the 10$^{th}$ and the 90$^{th}$ percentiles; one out of two representative experiments is shown.

FIG. 4: BCG zmp1 protective efficacy in a mouse mortality model. Groups of mice vaccinated with BCG, BCG zmp1 or untreated (control) were challenged with *M. tuberculosis* and survival was monitored.

EXAMPLES

Example 1

Materials and Methods

Mycobacterial Strains and Growth Conditions

*Mycobacterium bovis* BCG were grown on Middlebrook 7H10 agar plates supplemented with oleic acid albumin dextrose catalase (OADC) (Becton Dickinson), on Dubos agar, in liquid 7H9 medium supplemented with OADC in the presence of Tween 80 (0.05%) or in Dubos broth and incubated at 37° C.

The construction of the BCG zmp1 knock-out mutant has been described previously (Master et al., supra). Briefly, a 4.4 kbp NotI fragment comprising *M. tuberculosis* zmp1 (Rv0198c) and its flanking region was isolated from BAC clone Rv165 (Brosch et al. *Infect. Immun.* 66, 2221-2229 1998), parts of zmp1 (770 bp) were deleted by NheI digestion and substituted by a kanamycin resistance cassette. The resulting suicide vector was transformed into BCG strain 1721, selection was done on 7H10 agar supplemented with OADC in the presence of appropriate antibiotics (Sander et al., rpsL+: a dominant selectable marker for gene replacement in mycobacteria. *Mol. Microbiol.* 16, 991-1000, 1995). Replacement of chromosomal zmp1 locus by the inactivated allele was demonstrated by Southern blot analysis.

Immunisation of Mice for Analysis of DTH, Splenocyte Proliferation, Cytokine Secretion and FACS Mice were immunised with different doses of BCG or BCG zmp1 by subcutaneous injections. The inoculum was diluted in buffered saline and the injection volume was 100 µl. After three weeks, the mice were challenged by injection of 5 µg tuberculin purified protein derivative PPD (Statens Serums Institut, Copenhagen, Denmark), dissolved in 50 µl saline, into the plantar side of the hind right footpad. Two days later, DTH reaction was analyzed by measuring the swelling of the footpad using a spring-loaded digital micrometer (Mitutoyo, Kawasaki, Japan).

For in vitro analysis of splenocyte proliferation and cytokine secretion, mice were euthanized and the spleens harvested four weeks after immunisation. Briefly, $6 \times 10^5$ RBC-free splenocytes were incubated in round-bottom 96-well culture plates with PPD, or the *M. tuberculosis*-derived antigens Ag85A (LTSELPGWLQANRHVKPTGS) and TB10.3 (GTHESNTMAMLARDG) in supplemented RPMI medium. After three days, supernatants were collected and frozen down for later analysis of IFN-$\gamma$ secretion by ELISA (R&D Systems, Abingdon, United Kingdom). The remaining cells were pulsed with 1 µCi $^3$H-labelled thymidine another 16 hours for analysis of proliferation by $\beta$-scintillation.

For FACS analysis mice were primed and boosted at four week intervals. Seven days later, the splenocytes were harvested for analysis of IFN-$\gamma$ synthesis by flow cytometry. Single-cell suspensions of approximately $2 \times 10^6$ RBC-free splenocytes were re-stimulated in 24-well plates and for 5 hours with 5 µg/ml PPD or 0.5 µg/ml phorbol 12,13-dibutyrate (PdBu; Sigma, Buchs, Switzerland) in the presence of 5 µg/ml Brefeldin A (Sigma). The cells were then washed, incubated on ice for five minutes with anti-CD16/CD32 in PBS/FCS 2% with 0.01% sodium azide for Fc-receptor blocking, and surface stained with anti-CD4 (FITC) and anti-CD8 (PerCP) antibodies on ice for 20 minutes. After fixation in protein-free PBS/PFA 1% for 10 minutes, and permeabilisation in PBS/NP40 0.1% for 3 minutes, the cells were stained for intracellular IFN-$\gamma$ (APC) in PBS/FCS 2% and on ice for 35 minutes. The samples were acquired on a FACS-Canto and analysed using the FACSCanto Diva software from BD Biosciences (San Jose, Calif.).

Vaccination Experiments

Female mice 8-10 weeks of age at the beginning of the experiment were used. Clump-free mid-log phase mycobacterial suspensions were generated and the inocula were estimated directly by microscopic examination of filtered mycobacterial suspensions in a conventional hemocytometer and adjusted to the desired concentrations. Enumeration of the inocula's bacilli was done by plating 3-fold serial dilutions and scoring micro-colonies and visible colonies after 3 and 20 days incubation at 37° C., respectively, confirming that the accuracy of CFU count estimation by microscopy was >90%. Mice were vaccinated by subcutaneous inoculation of $10^6$ CFU of BCG, BCG zmp1 or left untreated (saline control). Six weeks after vaccination mice were challenged with $10^2$ CFU of virulent *M. tuberculosis* H37Rv by aerosol infection using an inhalation exposure system (Glas-Col, Terre Haute, Ind.). To assess mycobacterial loads in spleens and lungs, 0.1 ml of serial 10-fold dilutions of whole organ homogenates from four individual mice per time point were plated onto agar, and colonies were counted after 18-20 days of incubation at 37° C. For survival curves 6-9 mice per group were used. Moribund animals were sacrificed.

Histopathology

Twenty two weeks after infection with *M. tuberculosis*, lung tissues were examined for pathology. Lung tissue (the middle right lobe) was frozen using a −60° C. to −20° C. temperature gradient in an electronic cryotome and serial 6-8 µm-thick sections were obtained across the widest area of the lobe. Sections were stained with hematoxylin and eosin and examined by an experienced pathologist.

Statistical Analyses

Non-parametric data were analysed using a two-sided Mann Whitney U test for two independent samples or a Kruskal-Wallis H test with Dunn's post test for three or more samples. A two-way analysis of variance (GLM univariate analysis of variance) was performed, with footpad swelling, IFN-$\gamma$ secretion, or proliferation as dependent variables and the BCG strain (+/−zmp1) or immunisation dose ($10^2$-$10^4$ CFU) as fixed factors. Prior to the ANOVA, the Levene's test for equality of error variances was calculated and if necessary, a power transformation was applied to the data to meet the equal error variances assumption. The significance level was set at 5%.

Example 2 zmp Deletion Increases the Immunogenicity of BCG

To analyse the role of Zmp1 in immunogenicity of BCG, mice were immunised with titrated doses of wild type and zmp1 deficient strains. Measuring DTH response upon a footpad challenge with PPD, a different threshold for induction was observed for the two vaccine strains. While an inoculum of $10^3$ CFU of the wild type strain was required to produce significant footpad swelling, one tenth of this dose was sufficient to induce an equivalent response with the zmp1 mutant, maximal footpad swelling was observed between $10^4$ and $10^5$ CFU (data not shown). We further analysed the degree of footpad swelling at inoculums of $10^2$-$10^4$. As shown in FIG. 1, the zmp1 mutant induced a significantly stronger DTH response than did the BCG wild type at $10^3$ (P=0.0006; Mann Whitney) and $10^4$ (P=0.0262) CFU. The experiment was repeated, and a univariate analysis of variance of the combined data showed that independent of the size of the inoculum, BCG zmp1 caused a stronger DTH response than the wild type BCG (P<0.001).

Figure 2:
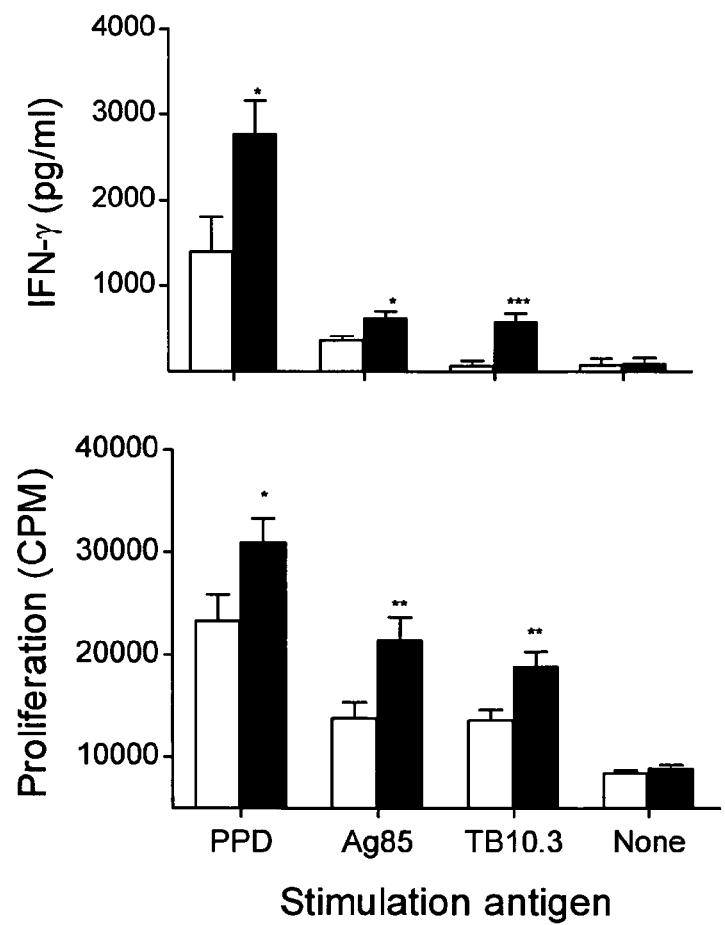

The increased immunogenicity of the zmp1 deficient BCG strain was associated with increased proliferative and cytokine secreting immune responses in vitro of splenocytes from mice immunised with either BCG wild type or BCG zmp1. FIG. 2 illustrates this at an inoculum of $10^3$ CFU, splenocytes from BCG zmp1 immunised mice showed significantly more IFN-$\gamma$ production than did the wild type after re-stimulation in vitro with PPD (P=0.0147 by Mann Whitney) or the *M. tuberculosis* antigens Ag85A (P=0.0133) or TB10.3 (P=0.0005). Similarly, cell proliferation was significantly increased in cells from mice immunised with BCG zmp1 (FIG. 2). A two-way ANOVA applied on all data, independent of the in vivo BCG dose or the type of antigen used for re-stimulation in vitro, revealed that the zmp1 mutant caused more efficient IFN-$\gamma$ secretion (P=0.023) and proliferation (P<0.001) than did wild type BCG.

Figure 3:
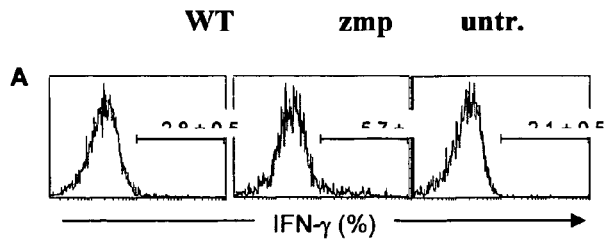
Figure 3:
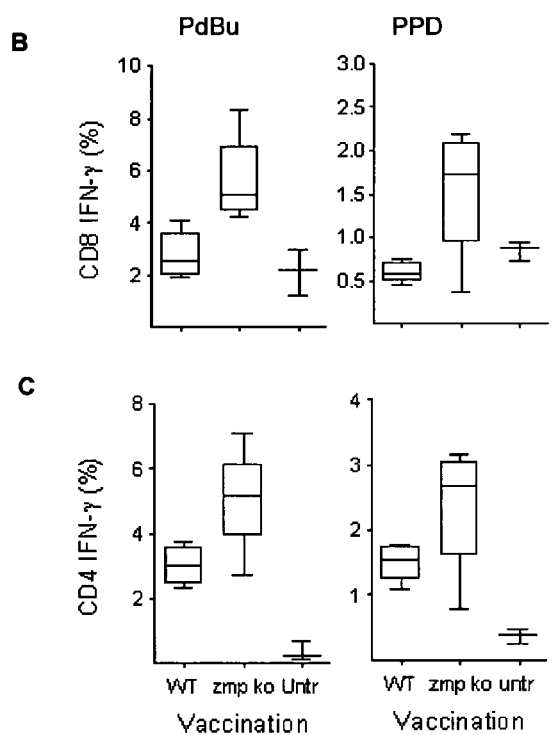
Figure 4:
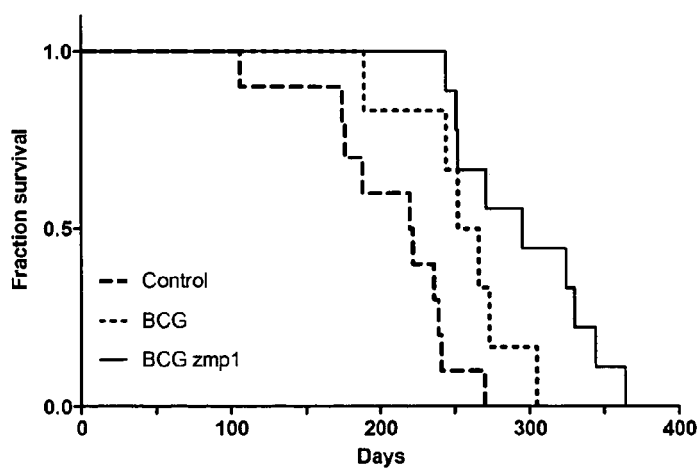

To analyse whether the IFN-$\gamma$ secretion derived from CD8 or CD4 positive T cells, splenocytes from immunised mice were stained and analysed by flow cytometry. Both T-cell subsets were able to produce IFN-$\gamma$ with frequencies as high as 7-9% (FIG. 3).

However, when comparing the frequencies of CD8 IFN-$\gamma$ producing cells in BCG-vaccinated mice to those of untreated mice, the wild type did not significantly differ from background levels as analysed by the Kruskal-Wallis test with Dunn's multiple comparison test (P>0.1). In contrast, the BCG zmp1 produced significant levels of IFN-γ for both CD4 and CD8 T cells when re-stimulated with either PdBu or PPD (P<0.05). A direct comparison of the two BCG strains showed that independent of the T-cell subset (CD4 or CD8) or of the re-stimulation antigen (PdBu or PPD), BCG zmp1 caused a strongly increased IFN-γ production.

Example 3 zmp1 Deletion Increases Protective Efficacy of BCG

The protective efficacy of *M. bovis* BCG zmp1 mutant was tested in a mouse model of tuberculosis. Groups of mice (C57BU6) were immunised by subcutaneous injection of BCG, BCG zmp1 mutant or left untreated. After six weeks mice were challenged with a low dose ($10^2$ CFU) of *M. tuberculosis* H37Rv by aerosol infection and CFU, lung pathology and mortality were monitored. Three weeks after aerosol challenge, lungs of control mice contained high numbers of *M. tuberculosis*. Vaccination reduced the bacterial burden in lungs and in the spleen by approximately 1 to 2 logs in the first three weeks of infection. Between three and twenty-two weeks after challenge mice were able to control the infection, and CFU counts stabilized.

Twenty-two weeks after infection, lung sections from all three groups of animals (unvaccinated control, BCG vaccinated, BCG zmp1 vaccinated) revealed areas of the lung parenchyma with reduced open alveolar space, variable widening of alveolar walls and macrophages filling the airspaces, with levels of non-specific diffuse inflammation affecting the lung parenchyma being lowest in BCG zmp1 vaccinated mice. Lymphocytic infiltrates, present around blood vessels and in juxtaposition of bronchiolar epithelia, were increased in the vaccinated groups compared to the unvaccinated control, and most pronounced in the BCG zmp1 vaccinated animals. On scanning magnification, the lymphocytic infiltrates in BCG zmp1 mice were the most dense with a tendency to confluence, while unvaccinated controls and BCG vaccinated animals had less dense lymphoid infiltrates with only small aggregates. To further quantify the extent of the lymphocytic infiltration in the different groups of animals, a morphometric approach was chosen, using AnalySIS-system (Olympus, Switzerland). In each animal lung section, 20 lymphocytic aggregates were identified. The mean diameter of lymphoid infiltrates was measured and the portion of lymphoid infiltrates/lung section was calculated. The mean diameter in the BCG zmp1 vaccinated group was 0.31 mm compared to 0.13 mm in BCG wt and 0.18 in the control group. Also, the percentage of lymphoid aggregates per lung section was increased in BCG zmp1 (7.2%), compared to BCG wt (1.85%) and control animals (2.2%).

The biological effect of zmp1 disruption on protective efficacy of BCG was further investigated in mice by analysis of mean survival times (MST) after infection. The results in FIG. 4 show that unvaccinated mice began to die 106 days post challenge and all of the unvaccinated controls were dead after 270 days, BCG vaccinated mice began to die by day 189 and the last mouse deceased at day 305, BCG zmp1 immunised mice started to die at day 244 and the last mouse died at day 364. MST was 203.8+/−13.9 days for control mice, 254.8+/−15.7 days for BCG vaccinated and 297.1+/−15.0 days for BCG zmp1 immunised mice (log rank BCG vs. unimmunised p=0.02; BCG zmp1 vs. BCG p=0.082; BCG zmp1 vs. unimmunised p=0.00009). Compared to BCG the BCG zmp1 mutant was nearly twice as effective in prolonging survival (ΔMST to unvaccinated controls 94 days for BCG zmp1 vs. 51 days for BCG); hazard ratios (HR) BCG vs. unimmunised=33% and p=0.032; BCG zmp1 vs. BCG HR=26% and p=0.01; BCG zmp1 vs. unimmunised HR=11% and p=0.000001.

The invention claimed is:

1. A method for prophylactically immunizing a patient at risk of becoming infected with *M. bovis* or *M. tuberculosis*, comprising:

administering to the patient a pharmaceutical composition comprising an active substance comprising at least one live mycobacterium of the *M. tuberculosis* complex, wherein the function of the zmp1 gene (zinc metalloprotease 1 gene) is at least partially inactivated and optionally a pharmaceutically acceptable excipient.

2. The method according to claim 1, wherein the patient is human.

3. The method according to claim 1, wherein the function of the zmp1 gene is fully inactivated.

4. The method according to claim 1, wherein the patient is at risk of an infection of *M. tuberculosis.*

5. The method according to claim 1, wherein the patient is at risk of an infection of *M. bovis* BCG.

* * * * *